United States Patent [19]

Arant

[11] 4,045,872
[45] Sept. 6, 1977

[54] ANALOG MODULE FOR RECONVERSION OF JAW MOVEMENT INFORMATION

[76] Inventor: Gene W. Arant, 2444 Jupiter Drive, Los Angeles, Calif. 90046

[21] Appl. No.: 558,284

[22] Filed: Mar. 14, 1975

Related U.S. Application Data

[63] Continuation-in-part of Ser. No. 419,641, Nov. 28, 1973, abandoned.

[51] Int. Cl.² .............................................. A22C 7/00
[52] U.S. Cl. ...................................................... 32/32
[58] Field of Search .......................... 32/32, 19, 20, 21

[56] References Cited

U.S. PATENT DOCUMENTS

| 3,048,923 | 8/1962 | Franwick | 32/32 |
| 3,206,852 | 9/1965 | Swanson | 32/32 |

*Primary Examiner*—Robert Peshock

[57] ABSTRACT

An analog module for use with a dental articulator is formed as a unitary structure having a pair of laterally spaced simulated fossae. The module is formed with reference openings in the undersides of the fossae, and it is then placed in a reconverter machine where the reference openings are enlarged to represent the three-dimensional jaw movement characteristic measured from a particular patient. Thereafter the module is attached to the upper frame of an Arkon type articulator where the enlarged openings reproduce the jaw movement pattern of the patient.

The module is provided with a fixed three-dimensional reference for establishing a predetermined reference position when it is placed in the articulator, and establishing the same reference position when it is previously placed in the reconverter machine. The module also has hinge axis alignment means engagable by pointers of a transfer face bow for aligning dental casts in the articulator.

The method of reconverting jaw movement information is characterized by the fact that the two fossae simulating the socket portions of the temporomandibular joints are at all times in the process treated as parts of an integral unit; i.e., the upper jaw structure is simulated as a unit both with regard to three-dimensional position referencing, inserting the dynamic movement information, and replaying the dynamic information.

The reconversion method is further characterized by the fact that any error or discrepancy between the three-dimensional reference position information of the patient and that of the analog module is compensated for at the input side of the reconverter.

18 Claims, 27 Drawing Figures

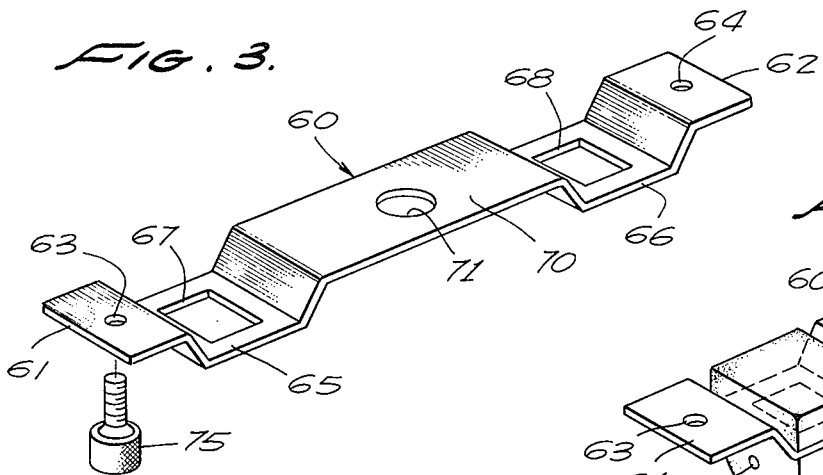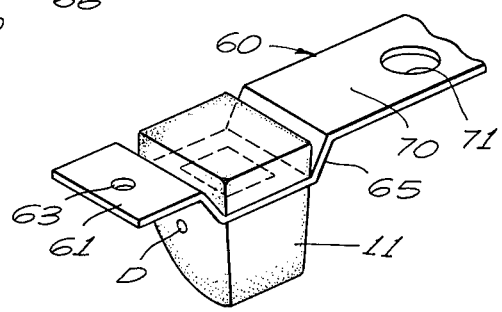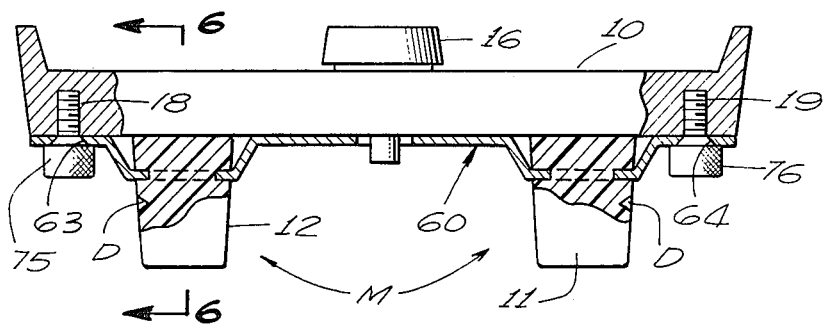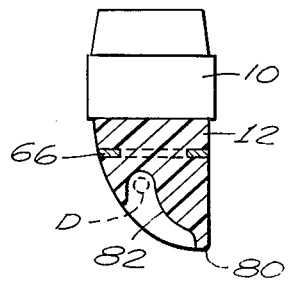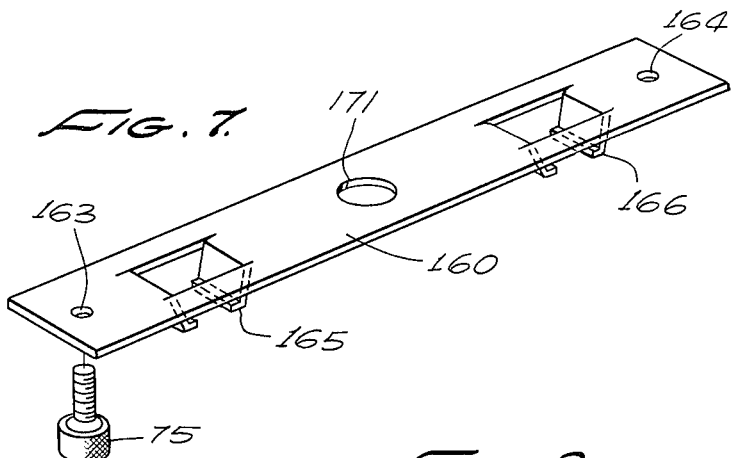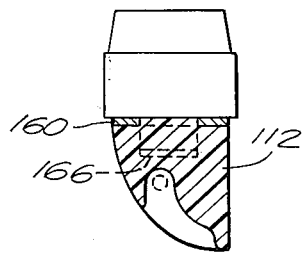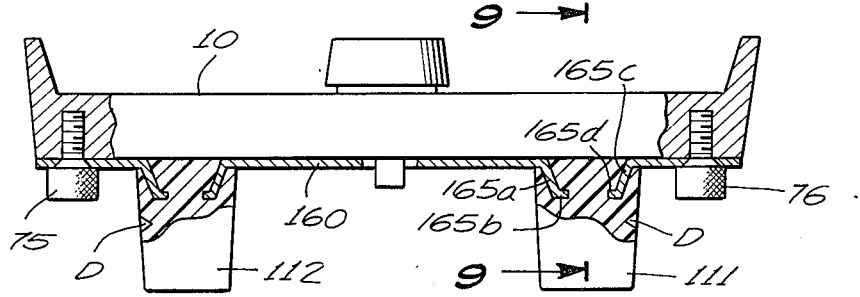

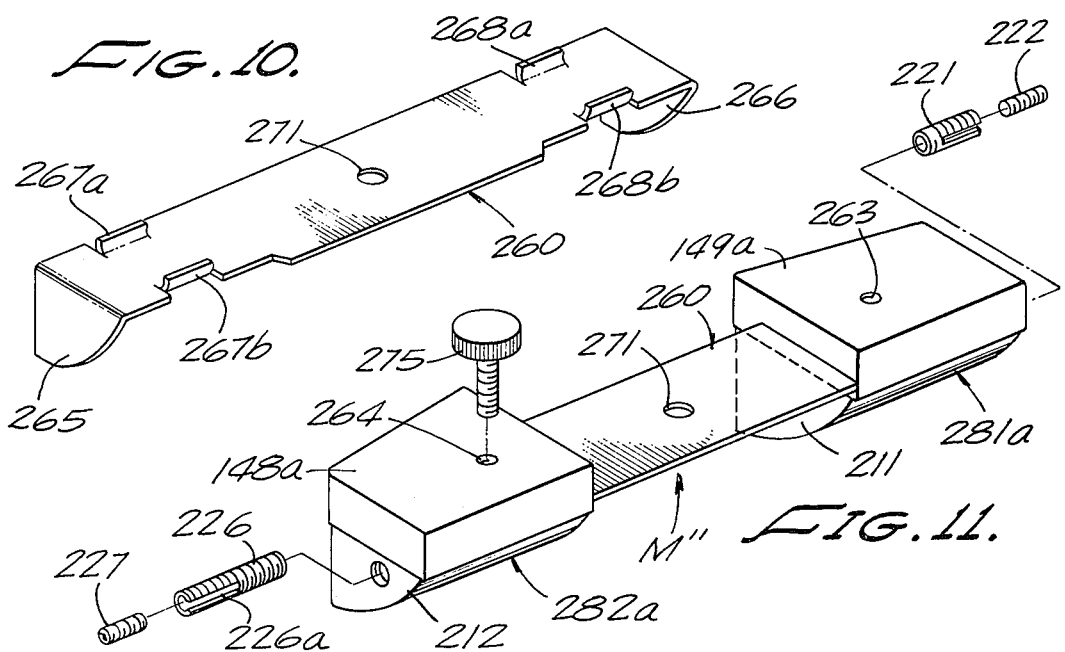
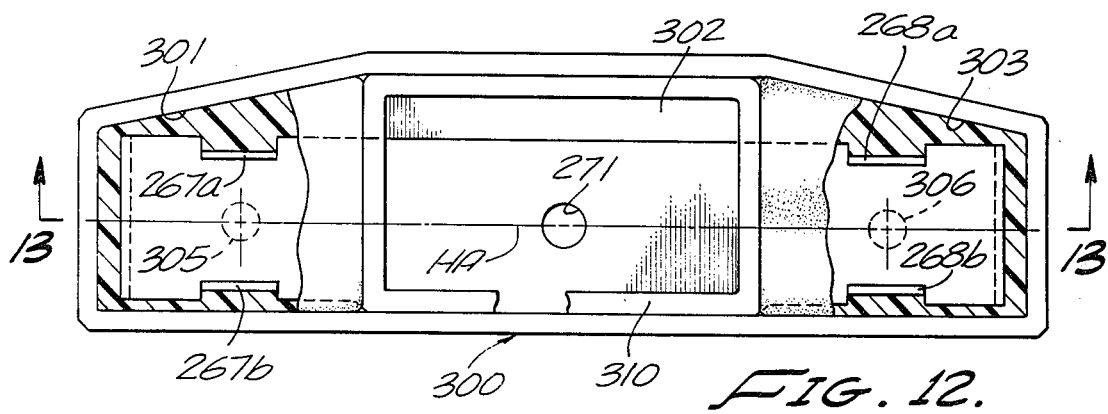
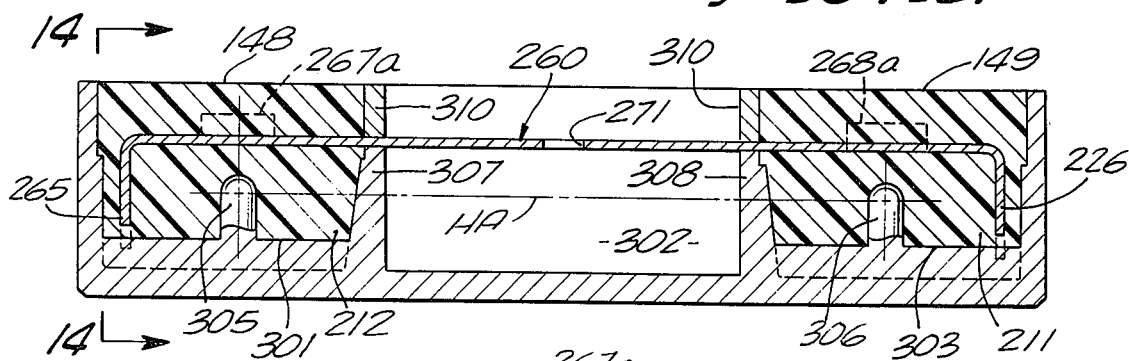
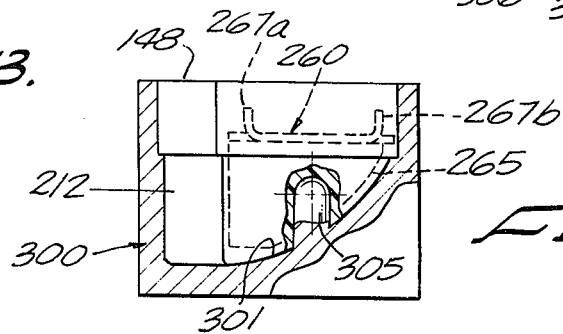

4,045,872

ANALOG MODULE FOR RECONVERSION OF JAW MOVEMENT INFORMATION

RELATED APPLICATION

This application is a continuation-in-part of my prior copending application Ser. No. 419,641 filed Nov. 28, 1973 and now abandoned.

BACKGROUND OF THE INVENTION

Successful use of the indirect method of dentistry involves equipping a dental articulator so as to accurately represent the chewing mechanism of a particular patient. Simulating the tooth structure with dental models or casts has long been a well-known procedure. It has also been well-known to utilize a transfer face bow for aligning the casts in the articulator. Simulating the action of the temporomandibular joints, however, has been a far more difficult and complex problem.

When the jaw movement characteristic of a patient is measured outside his head, the information as measured appears in a strange mixture of amplified and diminished magnitudes. The information must be reconverted in order to return its various portions to their original magnitudes, or nearly so, depending upon whether or not the "intercondylar width" of the patient is to be precisely reproduced in the articulator. The work of Robert L. Lee, D.D.S., of Colton, California, has established that this reconversion can be performed as an analog computation function. This work is described in Dr. Lee's articles in the August and November, 1969 issues of The Journal of Prosthetic Dentistry; and in U.S. Pat. Nos. 3,452,439 and 3,694,919.

The concept has also been advanced that it is unnecessary and uneconomic to precisely reproduce the "intercondylar width" in the articulator, and that it is instead preferable to utilize a pair of simulated fossae having a fixed lateral separation therebetween. The use of this concept in conjunction with Dr. Lee's analog reconversion procedure has been described in the publication "The Dentonamics System — January 1973" published by Dentonamics Corporation of Inglewood, California.

The present invention assumes that the jaw movement characteristic of a patient can be accurately recorded, either in mechanical form as shown by Dr. Lee, or in electronic form as shown by the work of others. The present invention is concerned with the mathematical theory of the information reconversion, and with providing an analog module as the most economical mechanization both for receiving the reconverted information in the reconverter and then for subsequently replaying or reproducing that information in the articulator.

PRIOR ART

Applicable prior art includes the references cited in the preceding paragraph. Also of interest is applicant's U. S. Pat. No. 3,854,208, which discloses a three-dimensional position adjustment mechanism.

SUMMARY OF THE INVENTION

The basic concept of the present invention is that only one three-dimensional alignment procedure is utilized in conjunction with the dynamic information reconversion or transfer process. This one alignment is accomplished on the input side of the reconverted machine. Specifically, the single analog module which incorporates both of the simulated fossae in fixed spatial relationship is aligned in the three-dimensional reference position it will later assume in the articulator, and at the same time is aligned with the three-dimensional reference information derived from the patient. Then the dynamic movement information derived from the patient is utilized for manipulating the analog module so as to enlarge the reference openings in the underside of its simulated fossae so as to represent the jaw movement characteristic of the particular patient. Thereafter the analog module is simply detached as a single unit from the reconverter machine and then is attached as a single unit to the articulator.

It is believed that the present invention provides both the mathematically simplest method for accomplishing the dynamic information reconversion, and also a simple mechanism for carrying out the method which is easy and inexpensive to manufacture and to use.

Further in accordance with the present invention, the design of an articulator for other purposes or in view of other considerations is made essentially independent of the problem of reproducing jaw movement information, since the design of the articulator to accept the analog module is essentially independent of its design characteristics used for other purposes.

DRAWING SUMMARY

FIG. 3 is a perspective view of a support member;

FIG. 4 is a fragmentary perspective view of the support member with one analog block attached;

FIG. 5 is an elevational view, partially in cross-section of the analog module when attached to an articulator frame;

FIG. 6 is a cross-sectional view taken on the line 6—6 of FIG. 5;

FIG. 7 is a perspective view of an alternate form of support member;

FIG. 8 is a view like FIG. 5, but showing the alternate design of the analog module;

FIG. 9 is a cross-sectional view taken on the line 9—9 of FIG. 8;

FIG. 10 is a perspective view of a third form of support member or strap;

FIG. 11 is an exploded perspective view of the presently preferred form of the analog module, incorporating the strap of FIG. 10;

FIG. 12 is a plan view, partially in cross-section, of a mold in which the module of FIG. 11 is being fabricated;

FIG. 13 is a vertical cross-sectional view of the mold with module contained therein, taken on line 13—13 of FIG. 12;

FIG. 14 is a cross-sectional view of the mold and module taken on line 14—14 of FIG. 13;

FIRST EMBODIMENT

(FIGS. 1-6)

Reference is now made to the drawings and particularly to FIGS. 1 through 6, inclusive, illustrating a first embodiment of the invention, an analog module M.

Figure 2:
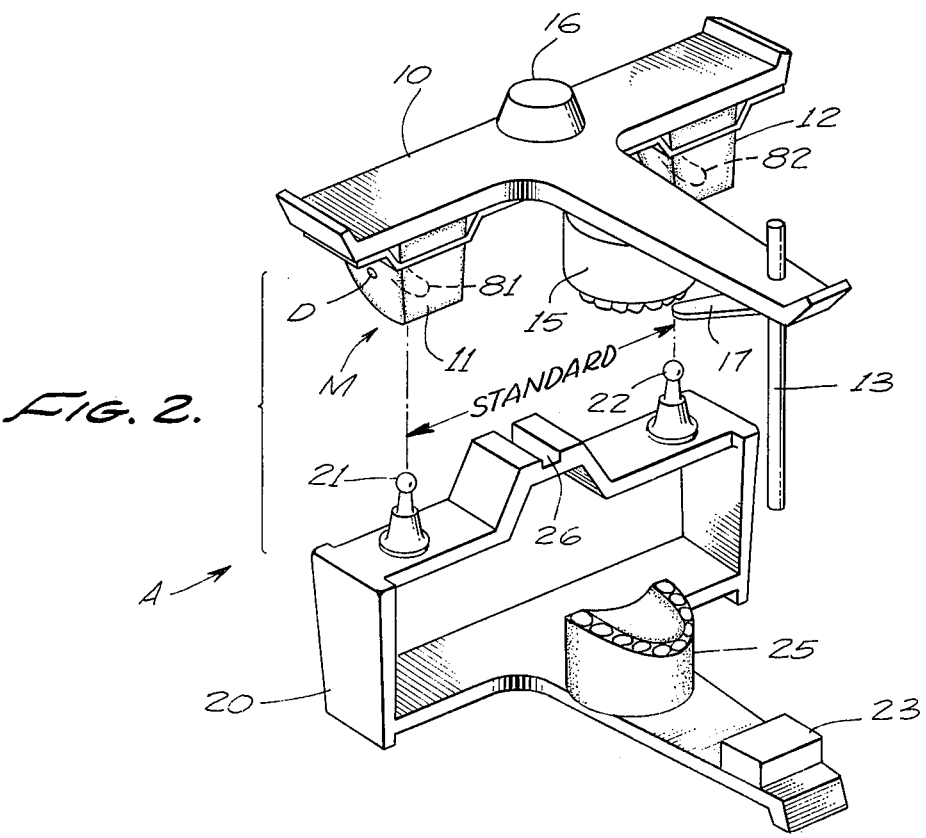
FIG. 2 is an exploded perspective view of a dental articulator in which the present invention is used.

By way of background information the dental articulator shown in FIG. 2 will first be described. The articulator A includes an upper frame 10 and a lower frame 20. Mounted on the lower frame 20 and a pair of spheres 21, 22 which are sometimes referred to as "simulated condyles" and which are characteristic of an Arkon articulator. These spheres are separated by a standard center-to-center distance which may, for example, be 110 millimeters. Also attached to lower frame 20 is an incisal rest block 23. The lower cast is identified by numeral 25. A centric reference groove located intermediate to the spheres 21, 22, is identified by numeral 26.

Attached to upper frame 10 is analog module M which includes a pair of simulated fossae or analog blocks 11, 12 shown in dotted lines. The upper cast is identified by numeral 15. An incisal rest pin 13 is carried by the upper frame, and cooperates with the rest block 23. A centric lock device 16 cooperates with reference groove 26. An orbital plane indicator 17 is also carried by the upper frame 10, and is utilized in conjunction with dimples D of the analog blocks.

A detail of the articulator which is shown only in FIG. 5 is the threaded openings 18, 19, which are formed in the lower surface of upper frame 10 for the purpose of removably attaching the analog module thereto.

The analog module M of the present invention, shown in perspective in FIG. 1, will now be described. It includes the support member 60, best seen in FIG. 3, and the simulated fossae or analog blocks 11, 12.

Support member 60 is an elongated metallic member having essentially the configuration of a flat strap. Its ends are identified as 61, 62, respectively. Adjacent the ends are attachment holes 62, 64, respectively. Just inside its end portions the strap 60 is deformed downwardly to form a pair of pedestals 65, 66. Openings 67, 68 are formed in the respective pedestals. An intermediate portion 70 of the strap extends between the pedestals, and contains an additional hole 71 which is located at the exact longitudinal center of the strap.

Analog blocks 11, 12 are made of a hard plastic material and are integrally cast in such a way as to be immovably supported in the openings 67, 68, respectively. Thus, the block 11 as shown in FIG. 4 extends through the opening 67 and partially envelops the upper and lower surfaces of the pedestal 65 to provide a rigid and permanent securement. Block 12 is mounted in similar fashion. Alternatively, the blocks may be made of any hard material that is capable of being milled to precise tolerance.

Intermediate portion 70 of the mounting strap 60 lies at the same elevation as the end portions 61, 62 so that all of these portions of the mounting strap will simultaneously engage the underneath flat surface of the articulator upper frame 10. The central hole 71 receives the centric lock device 16 and permits it to cooperate with groove 26, as previously described.

Referring now to FIG. 5, it will be seen that the attachment holes 63, 64 have a larger diameter on the bottom side of strap 60 than they do on the top side. The peripheral walls of these holes are tapered in order to provide a reliable and precise centering action. Thumb screws 75, 76 having tapered head portions, are passed through the attachment holes 63, 64, respectively, and engage the threaded openings 18, 19 respectively in the articulator upper frame 10, in order to secure the analog module M in a fixed position relative to the articulator upper frame.

It is preferred that the upper surface of the analog blocks 11, 12 be cut off to form a smooth flat surface which lies on the same plane as the upper surfaces of the strap portions 70, 61, and 62. This configuration of the module is shown in FIGS. 4 and 5. However, the upper ends of the blocks may if desired be cut shorter so that the entire mechanical support for the analog box is then provided by the metal strap 60.

By way of further background information the reconverter instrument T shown in FIG. 1 will now be described. Instrument T includes an upper frame 30 and a lower frame 40. Locigraph blocks 31, 32, 33 which carry the originally recorded jaw movement information are attached to respective extremities of the upper frame 30. A centric indicator device is identified by numeral 36. Threaded holes 38, 39 receive the thumb screws 75, 76, respectively, for securing the analog module M in position.

On the lower frame 40 a set of tracing pins 41, 42, 43 are mounted on respective extremities of the frame and cooperate with the blocks 31, 32, 33 for reproducing the original jaw movement information. A centric reference groove 46 is also provided on the lower frame. A pair of drills 51, 52 are also mounted on lower frame 40, and these drills are pointed vertically upward and their upper ends have a precisely hemispherical configuration. The lateral distance between the centers of these drills is a standard distance, which precisely coincides with the standard distance between the spheres 21, 22 of the articulator, and hence may typically be 110 millimeters. The drills or mills 51, 52 may be somewhat loosely referred to as "condyle drills" or "condyle mills".

MODE OF OPERATION

Figure 1:
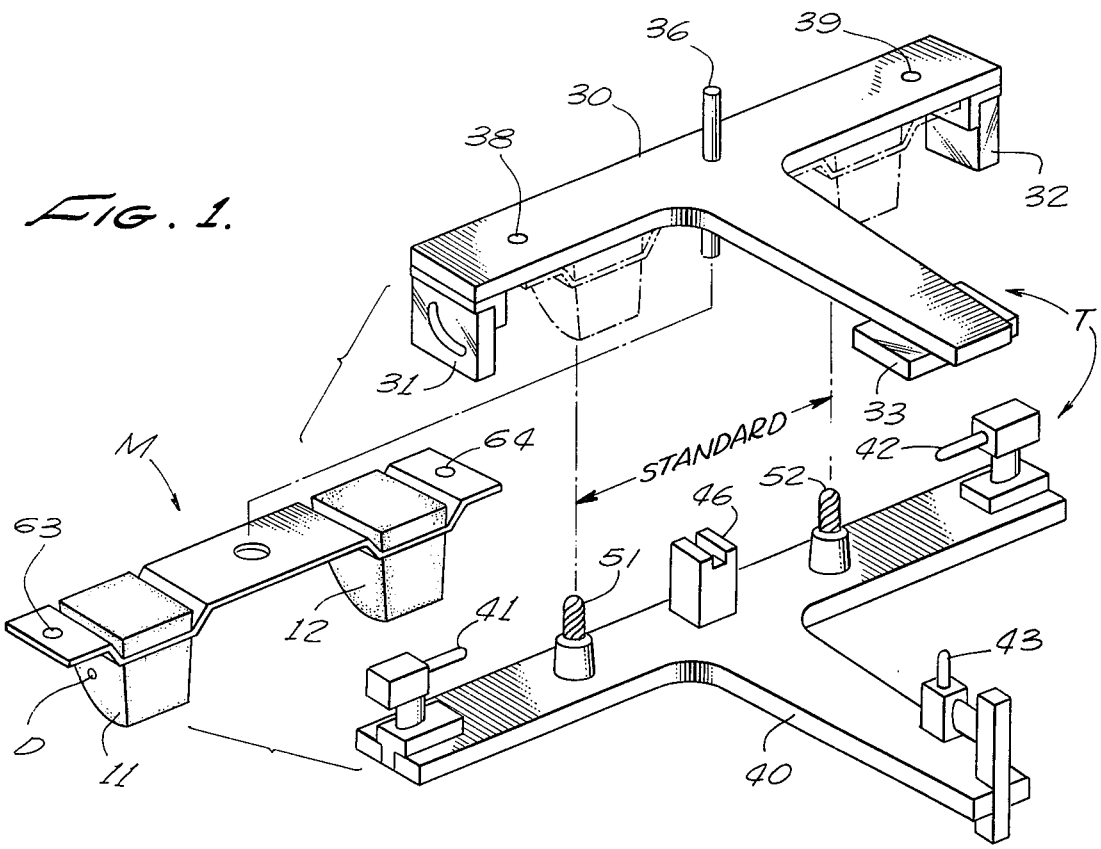
FIG. 1 is an exploded perspective view of a reconverter instrument in which the present invention is utilized.

The analog module M is first attached to the upper frame 30 of the reconverter instrument T, as shown in FIG. 1 by means of dotted lines. Operation of the reconverter instrument causes a pair of openings to be formed in the lower sides of the blocks 11, 12, which openings cooperatively represent the jaw movement pattern of a particular patient. Thus, as shown in FIG. 6 the lower surface 80 of block 12 contains an opening 82, whose shape is characteristic of a particular jaw movement pattern. A similar opening 81, shown only by dotted lines in FIG. 2, is formed in block 11.

As shown in FIG. 6 one portion of opening 82 has a hemispherical end whose radius center, together with the radius center of a portion of opening 81, defines the hinge axis of the module. Dimples D on the external lateral sides of blocks 11, 12 are also located on the hinge axis. However, because of error or discrepancy between the three-dimensional reference of the patient as reflected in the recordings in locigraph blocks 31, 32, 33, and the three-dimensional reference of the articulator, the hinge axis of module M is determined empirically. Separate means, not shown in FIG. 1, are provided for adjusting the three-dimensional alignment of pins 41, 42, 43 relative to the drills 51, 52. That is, the module is built without any axis identification; initial reference openings in blocks 11, 12 are formed by instrument T so as to correspond with the centric reference of the locigraph blocks; and thereafter dimples D are added on the same empirical basis.

Thumb screws 75, 76 are removed so as to detach the analog module M from the upper frame 30 of transfer instrument T. Module M is now inserted into articulator A where it is attached to upper frame 10. Thumb screws 75, 76 are again used for this purpose as shown in FIG. 5.

The attachment holes such as 63, 64 may be located inside the respective pedestals and the threaded openings 38, 39, and 18, 19 are then relocated accordingly. If attachment is made directly in the retaining means the thumb screws 75, 76, are positioned above the instrument frame. Other means of attachment may also be employed.

In order to make articulator A useful for purposes of dentistry it is necessary to incorporate the dental casts 15, 25 therein and this cannot be done until after the analog module M has been attached in its proper location. It then becomes necessary to utilize a transfer face bow in conjunction with dimples D of the analog blocks and the plane indicator 17, in order to accurately position the casts 15, 25. A transfer face bow as disclosed in Patent No. 3,854,208 has the advantage of being able to accommodate the face width adjustment.

SECOND EMBODIMENT (Figures 7-9)

Reference is now made to the drawings FIGS. 7 through 9, inclusive, illustrating a second embodiment M' of the invention. The elongated metallic support member 160 is in the form of a flat metal strap having precisely the same upper surface elevation throughout its length. The threaded attachment holes 163, 164, and the center hole 171, may be identical to the corresponding holes of the previous embodiment. Pedestals 165, 166, however, are constructed somewhat differently from those previously shown. Each pedestal is formed by transversely cutting the lateral central portion of the strap to form two tongues behind the lateral cut, and then bending the tongues downwardly. The blocks 111, 112 are integrally cast in such a way as to extend through the opening provided by the respective pedestal and also to partially envelope the tongues from which the pedestal is formed. The precise configuration is best seen in FIG. 8 where it is shown that the tongues of each pedestal are tapered towards each other and have small inwardly turned flanges on their lower ends. Thus, in pedestal 165 the tongues are identified as 165a, 165c, while the in-turned flanges are identified as 165b, 165d, respectively.

As in the first embodiment, the location of the openings in blocks 111, 112 is empirically determined in the reconverter instrument, and dimples D indicating the hinge axis of the module are formed thereafter.

ADVANTAGES

An important advantage of the first two embodiments of the present invention is that it greatly increases the precision of the system. Heretofore the analog blocks have been individually positioned, first in the reconverter or transfer instrument and later in the articulator. Any method of individual positioning is time consuming and inaccurate, and simply cannot guarantee that the precise relative positions of the openings 81, 82 remain unchanged. In accordance with the present invention, however, the unitary construction of the analog module insures this result.

A further advantage of the invention is that it avoids any possible mix-up of simulated fossae or analog blocks belonging to two different patients. The pair of blocks belonging to a particular patient are permanently fastened together and cannot be severed. By the same token, the necessity of identifying one block as being for the left hand side of the instrument and the other block as being for the right hand side of the instrument is avoided. There is only one possible location for fastening the analog module to either the reconverter instrument or the articulator hence confusion in this respect is avoided.

A further advantage of the invention is that patient identification procedures are simplified. It is no longer necessary to attach separate identifications to each of a pair of blocks, but rather a single identification can be attached to the module.

Yet a further advantage of the invention is a significant reduction in manufacturing costs as compared to the apparatus known heretofore.

However, the first two embodiments of the invention still require the prior art procedure of locating empirically, in the reconverter instrument, the initial reference openings in the under sides of the simulated fossae. Thereafter dimples D are formed in the external sides of the fossae to indicate the hinge axis of the module, and the openings in the under sides of the fossae are enlarged to represent the dynamic movement information.

PREFERRED EMBODIMENT (FIGS. 10-27)

According to the preferred form of the invention the analog module retains the features described in the first and second embodiments, and in addition the necessary means for identifying the hinge axis of the module, and aligning other portions of the instrumentation to it, are incorporated into the module during the original manufacturing process. Specifically, during the manufacturing process a pair of initial reference openings having hemispherical upper ends are formed in the under sides of the simulated fossae. The radius centers of these reference openings then define the hinge axis of the module. Means indicating the hinge axis of the module, and adapted for alignment of a transfer face bow therewith, are also formed on the external lateral sides of the fossae.

In order to carry out the preferred form of the invention it is necessary to construct the reconverter instrument in a different manner than previously described. The reconverter instrument of FIG. 1 holds the locigraph blocks 31, 32, 33 in fixed positions relative to the analog module M. The lower part of the instrument includes means, not shown in the drawings, for adjusting the three-dimensional position of the replay pins 41, 42, 43 (as a complete set whose relative positions are maintained in fixed relationship) relative to the mills 51, 52. That arrangement of the reconverter instrument cannot be used in accordance with the preferred form of the analog module of the invention.

For purposes of the preferred form of the invention the replay pins are held in fixed positions relative to the reconverter mills. The locigraph blocks are held in fixed positions as a unitary set and their position is adjustable relative to the position of the analog module M". The technique of holding the locigraph blocks in fixed position as a unitary set, and adjusting the position of that set relative to the simulated fossae of the reconverter instrument, was used by Dr. Lee and is shown in FIG. 56 of his U.S. Pat. No. 3,452,439. However, its use was discontinued about 1969.

Figure 20:
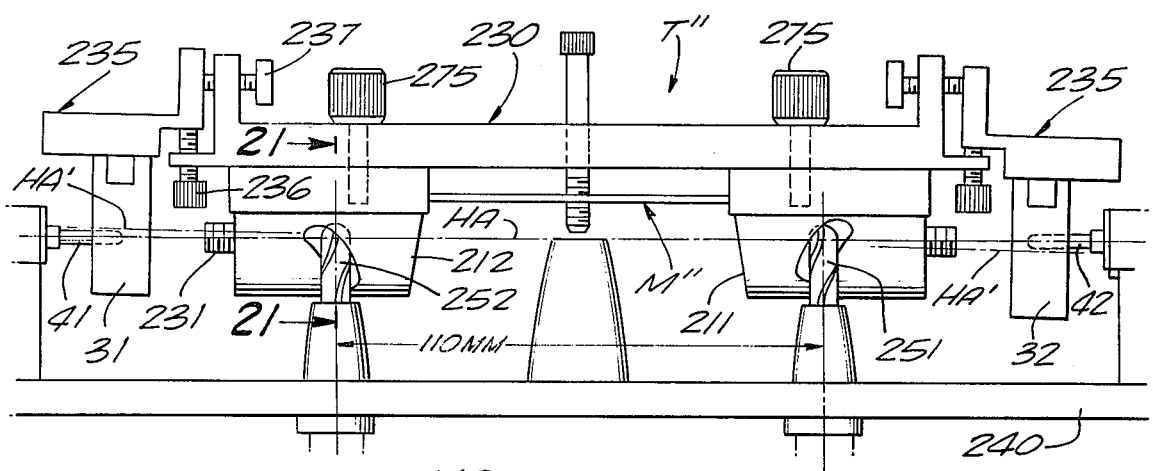
FIG. 20 is an elevational view of the module of FIG. 11 when positioned in a reconverter instrument.

Reference is made to FIG. 20 illustrating a modified reconverter instrument T". This instrument includes a central upper frame 230 from which the preferred form of the analog module M" is supported. It also includes a U-shaped outer upper frame 235, which holds the set of three locigraph blocks. Means ar provided for adjusting, in three-dimensions, the position of frame 235·relative to the position of frame 230. It is this arrangement of the reconverter instrument which makes it possible to incorporate the hinge axis identification into the analog module as it is being manufactured.

While the present drawings do not illustrate electronic measurement of the jaw movement information, it is nevertheless true that electronically sensed jaw movement information may be reconverted in the same manner as herein described with regard to the mechanically recorded information, permitting the advantageous utilization of the presently preferred form of the analog module of the present invention.

MATHEMATICAL THEORY

The presently preferred form of the invention is based upon a mathematical theory with regard to the relationship between the three-dimensional static reference information and the three-dimensonal dynamic movement information. It has been known in the prior art that an effort should be made to measure both the static and the dynamic information accurately, both on an independent basis and in relation to each other. The problem is the specific technique to be used, both in a mathematical sense and with regard to its mechanization.

Where the jaw movement information is reconverted in an analog computation process, as shown very clearly in the work of Dr. Lee and also shown marginally in the work of others in the field, a complete instrument system then includes three separate primary instruments: an instrument for measuring and/or recording the jaw movements; the analog reconverter; and the articulator for replaying or reproducing the information. The work of Dr. Lee demonstrated in actual practice, that the three-dimensional static reference of the original measuring or recording instrument is seldom, if ever, going to coincide with the three-dimensional static reference of the articulator. The three-dimensional static reference is known to gnathologists as the orbital-axis plane, but this description is insufficient. This reference is completed on the patient by a pair of marks on the temples, located as nearly as possible to the extended hinge axis, plus a third mark on the noze. These marks are tattooed for permanence. These three marks not only establish a plane, but they also establish the hinge axis, and they further establish a vertical plane of symmetry which is mid-way between the temple markings. The centric position of the mandible must also be established.

Where an Arkon articulator is used, having a pair of spheres on its lower frame, the existence of a hinge axis in the articulator then becomes clear indeed but this does not necessarily insure that the same thing really existed in the patient. As a matter of fact there are several theoretical reasons why the simulation established in the articulator will not precisely reproduce the movement action of the patient's jaws. Furthermore, even assuming that the instrument is theoretically capable of fully reproducing the patient's jaw action, it is nevertheless true that there is a certain mathematical probability of error in the original measurement made on the patient, both with regard to the static information and with regard to the dynamic information.

The preferred embodiment of the present invention is based upon two concurrent hypotheses. The first hypothesis is that the analog reconverter should not have a three-dimensional static reference of its own. It should have the static reference of the patient, or of the articulator, or perhaps both, but not any different or independent static reference. The second hypothesis is that the static reference of the articulator should be extended through the instrument system as far as possible, reaching as close as possible to the actual measurement of information on the patient. The application of this hypothesis means that the static reference of the reconverter should be the same as the static reference of the articulator, except at the very input of the reconverter. This second hypothesis is not based upon mathematical considerations, but upon considerations of the economics both of manufacture and of use of the instrumentation.

The information measured from the patient includes a portion which identifies the three-dimensional static reference of the patient, i.e., a pair of laterally symmetical points on the hinge axis as well as a third point indicating elevation of the orbital axis plane. When a mechanical recording in solid plastic blocks is used, this static reference portion of the information is easily identified. See the Lee U.S. Pat. No. 3,452,439. When the jaw movement information is sensed electronically it is also easily possible to identify the three-dimensional static reference portion of the information.

According to the present invention the analog module is aligned in the reconverter by placing the simulated fossae upon the drills (or mills) with the drill ends being received in the reference openings of the fossae. Then the three-dimensional reference portion of the jaw movement information of the patient is aligned with or adjusted to the existing position of the analog module. This involves making a three-dimensional adjustment to compensate either for measurement error, or for the theoretical inability of the articulator instrument to correctly represent the patient, or both. Then the dynamic movement information is fed to the reconverter, the drills being rotated to enlarge the reference opening so as to represent the jaw movement pattern of the patient.

DESCRIPTION OF FIGS. 10-27

Manufacture of the model M" will first be described.

As shown in FIG. 10 an elongated metal strap 260 has a central opening 271 formed therein. The end portions 265, 266 of the strap are bent over at a right angle to the main portion of the strap, and the rearward sides of these end portions as seen in FIG. 10 are arcuately curved. A short distance inwardly from the end portion 265 a pair of cut-outs 267a, 267b in the longitudinal edges of the metal strap are turned upwardly at 90° in parallel relationship to each other. A similar pair of cut-outs 268a, 268b a short distance inside the strap end 266 are also turned upwardly in parallel relationship.

A mold 300 (FIGS. 12 to 14) is used for the purpose of adding the simulated fossae to the strap 260. The mold 300 is in the form of a rather long, narrow, generally rectangular tray having a moderate depth. It has a pair of end cavities 301, 303 and a central cavity 302. Central cavity 302 is almost precisely rectangular while the end cavities 301, 303 are tapered to a lesser width on their extremities. A vertical pin 305 having a smoothly curved hemispherical upper end projects upwardly from the center of the bottom wall of cavity 301. A similar pin 306 projects upwardly in the center of cavity 303. The interior walls 307, 308 which separate the central cavity 302 from the end cavities are less than the full height of the mold, but considerably higher than the tops of the pins 305, 306. See FIG. 13.

Strap 260 is placed in the mold resting upon the walls 307, 308 and with its ends 265, 266 depending downwardly near the outer ends of the end cavities 301, 303. The arcuately tapered portions of the strap ends 265, 266 are bent toward the straight longitudinal wall of the mold, rather than towards its longitudinal tapered wall. The strap cut-outs 267a, 267b are then symmetrically positioned above and on opposite sides of the pin 305, while strap cut-outs 268a, 268b are symmetrically positioned above and on opposite sides of the pin 306.

A rectangular frame 310 (FIGS. 12 and 13) is then inserted into the upper portion of the central cavity 302 so as to gate off the end cavities and also to weight the strap 260 in place. Then suitable plastic material is poured into the end cavities and allowed to harden, forming the fossae 211, 212. As shown by dotted lines in FIG. 14, the curved edge of strap end 265 lies a short distance within the curved rearward surface of the fossa 212.

Figure 15:
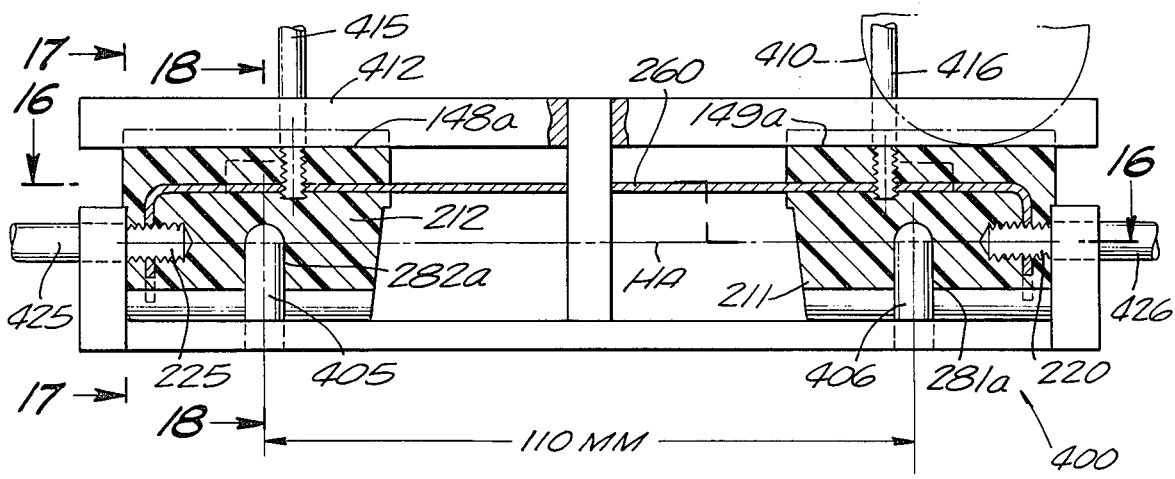
FIG. 15 is an elevation view of a drill jig used after the mold of FIGS. 12 through 14, to complete the manufacture of the module of FIG. 11.

After removing the module from the mold the next step is to use the drill jig or fixture 400 (FIGS. 15 through 18) in order to establish the three-dimensional referencing and indexing means for the module. The fixture 400 has a pair of pins 405, 406 extending up from its bottom wall, and which are of the same size and shape as the pins 305, 306 of the mold. The distance between pins is also precisely the same as the distance between spheres 21, 22 of the articulator, being preferably 110 mm between centers as indicated in FIG. 15.

This same distance between pins was, of course, used in the mold. The strap 206 with appended fossae 211, 212 is fitted into the fixture 400. Reference opening 281a in the under side of fossa 211 receives the pin 406 while reference opening 282a in the under side of fossa 212 receives the pin 405. See FIG. 15.

The fossae as originally formed include upper surfaces 148, 149 which extend far above the strap 260 (FIGS. 13 and 14). A grinding wheel 410 (shown in dotted lines in FIG. 15) is used in conjunction with fixture 400 to machine the surfaces down to a precisely finished level, and the lowered and precisely machined surfaces are identified as 148a, 149a. See FIGS. 15, 17, 18 and 19. These surfaces will later be used to precisely position the module against the under surface of an instrument upper frame, first the upper frame of the reconverter and then the upper frame of the articulator.

Figure 16:
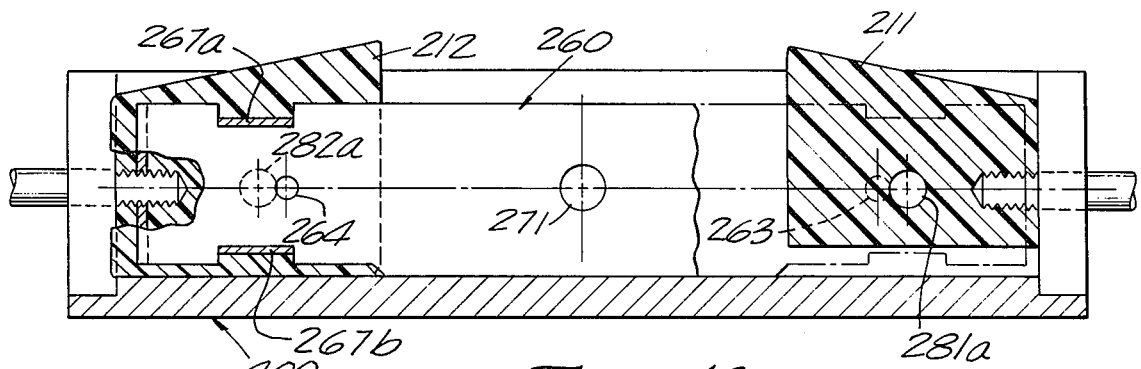
FIG. 16 is a cross-sectional plan view of the module and drill jig taken on the line 16—16 of FIG. 15.
Figure 17:
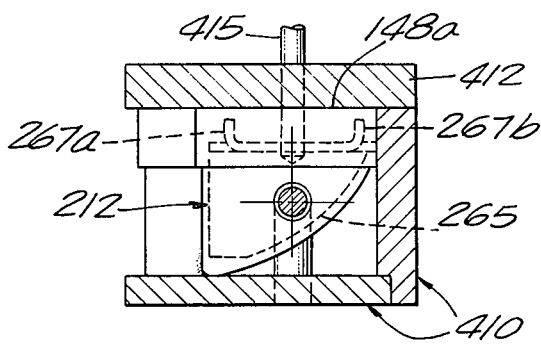
FIG. 17 is a cross-sectional elevational view of the module and drill jig taken on line 17—17 of FIG. 15.
Figure 18:
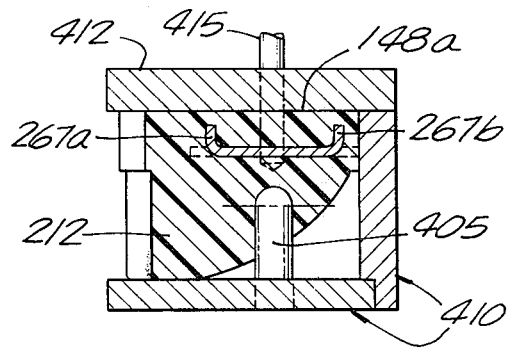
FIG. 18 is a cross-sectional elevational view of the module and drill jig taken on the line 18—18 of FIG. 15.

After the upper surfaces 148a, 149a of the module have been precisely machine finished, an upper member 412 of the fixture 400 is then placed upon them in a precisely controlled position for controlling the action of a pair of drills 415, 416. The drills 415, 416 drill holes through the upper portions of the fossae and also through the metal strap 260, each hole being centered between the corresponding pair of the ears 267a, 267b or 268a, 268b. The holes thus drilled are identified as 263, 264, respectively, as shown in FIG. 16. The lateral separation of these holes is preferably 100 mm. Therefore, the hole 264 formed in the upper surface of fossa 212 has its vertical center line located 5 mm towards the center of the module relative to the vertical center of the reference opening 282a which is formed in the under surface of the same fossa. And hole 263 is 5 mm inwardly from opening 281a in fossa 211.

Figure 19:
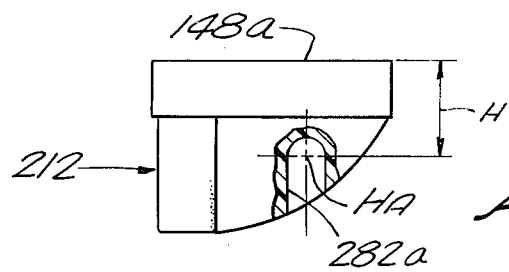
FIG. 19 is an end view, partially in cross-section of the completed module.

The radius centers of reference openings 281a, 282a identify the hinge axis of the analog module, internal of the module. As shown in FIG. 19 the machining of surfaces 148a, 149a provides a precise vertical distance H between the hinge axis and the machine surfaces. The machine surfaces in conjunction with holes 263, 264 provide a precise three-dimensional reference when the module is attached to the upper frame of an instrument. For purpose of such attachment the holes 263, 264 are preferably threaded, as shown.

It is also necessary, however, to provide an external indication of the hinge axis on the external sides of the simulated fossae. This may, if desired, be accomplished by forming dimples D such as used in the first two embodiments of the invention. If so, the dimples are then formed in the outer walls of the fossae while the module is held in place in the fixture 400.

Since the fossae have a fixed lateral separation in the module, the use of dimples D is not alone sufficient to accommodate for the adjustment between the face width of the patient (where hinge axis tatoo marks are measured with a transfer face bow) and the external width of the module. In conjunction with dimples D it may therefore be desirable to utilize a transfer face bow having the self-contained capability of making the face width adjustment, such as disclosed in applicant's previously mentioned U.S. Pat. No. 3,854,208.

Figure 23:
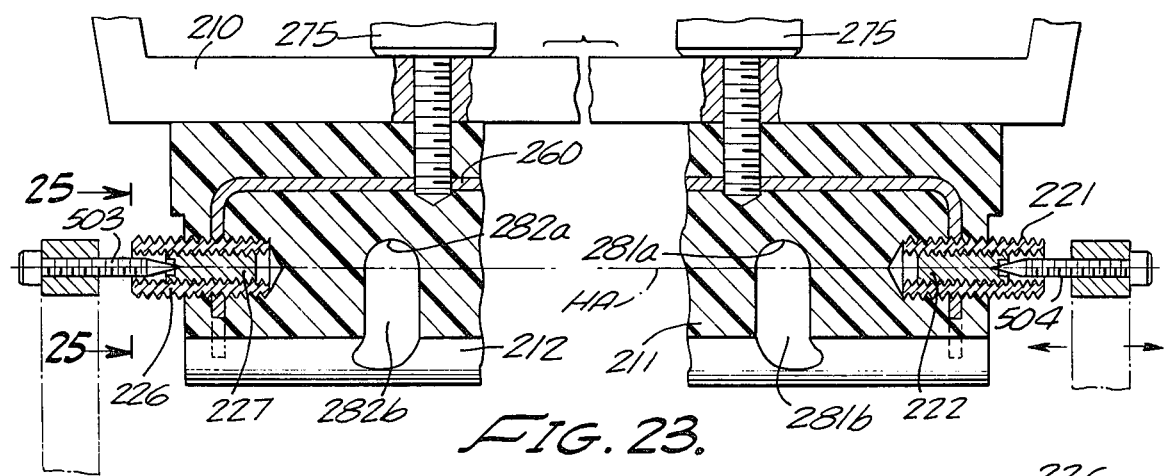
FIG. 23 is an elevation view, partially in cross-section taken on line 23—23 of FIG. 22.
Figure 24:
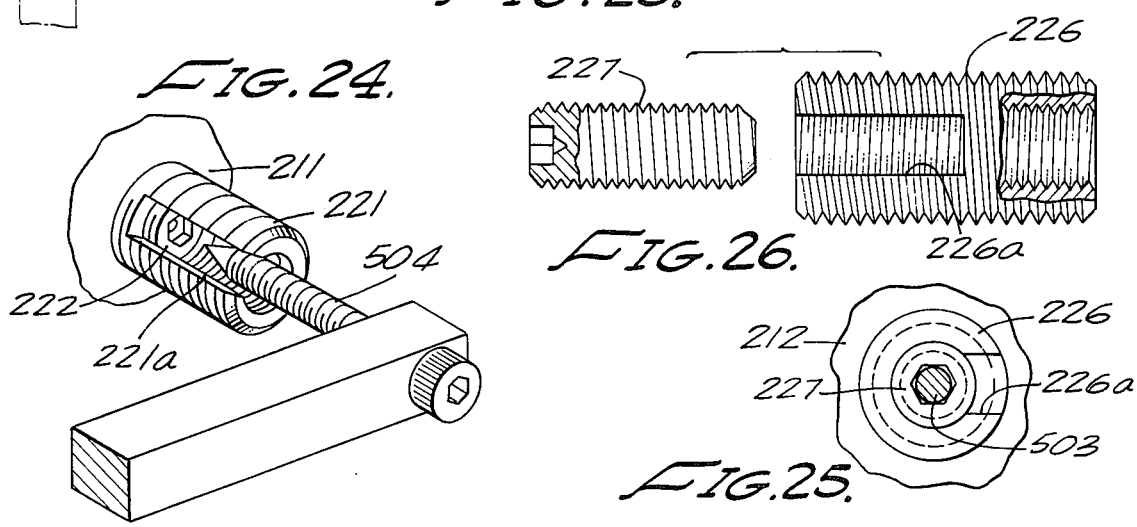
FIG. 24 is an enlarged perspective view showing attachment of a transfer face bow pointer to the analog module.

However, it may be preferred to utilize a conventional transfer face bow that does not have the capability of making the face width adjustment. With that end in mind the preferred analog module of the present invention is provided with the capability of making the face width adjustment. A drill 425 guided by an end wall of fixture 400 forms a threaded opening 225 in the fossa 212 which is concentric with the hinge axis HA of the module. A drill 426 guided by another end wall of fixture 400 drills a threaded opening 220 into the fossa 211 which is again concentric with the hinge axis HA. A threaded tube 226 is threadedly inserted into the opening 225, and a threaded tube 221 is threadedly inserted into the opening 220 (FIGS. 11, 20, 23). Threaded set screws 227, 222 are inserted into the tubes 226, 221, respectively.

Figure 26:
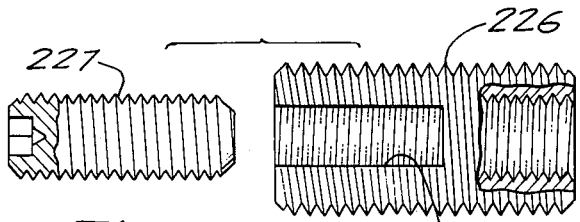
FIG. 26 is an exploded view, partially in cross-section, of one of the threaded tubes and threaded plugs of the analog module.
Figure 25:
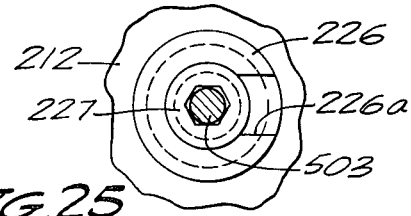
FIG. 25 is a fragmentary view, partially in cross-section taken on line 25—25 of FIG. 23.

Each of the threaded tubes is long enough to project some distance out from the threaded opening in which it is received. Furthermore, each of the threaded tubes in its projecting end has a circumferential portion removed. Thus the tube 226 has a longitudinal slot 226a in its outer end as shown in FIG. 11 and again in FIGS. 25 and 26.

The complete analog module M" is shown in FIG. 11 Fastening screws 275 used to engage the threaded openings 263, 264 are not necessarily part of the module itself.

USE OF RECONVERTER

In the reconverter T" of FIG. 20 the drills 251, 252 are supported on a fixed base 240. Analog module M" is fastened by means of the two screws 75 to the forward arms of a T-shaped center frame 230. With the drills not running reference openings 281a, 282a are positioned upon the upper ends of the drills. Not only does the hinge axis of the drills coincide with the hinge axis of the module, but the drills being the same diameter as the reference openings support the module and the T-shaped frame 230 in three dimensions.

The U-shaped frame 235 surrounds the ends of the T-shaped frame 230, being spaced therefrom both vertically and horizontally at each of the three potential points of contact, and is adjustably supported from the frame 230 by a set of three vertical screws 236 and a set of three horizontal screws 237. Locigraph blocks 31, 32, 33, similar to those shown in FIG. 1, are attached in fixed positions to the underside of U-frame 235. The playback pins 41, 42, 43, similar to those shown in FIG. 1, are attached in fixed positions on the frame 240.

The adjustment screws 236, 237 are all retracted before positioning frame 235 in place. The lateral pins 41, 42 are retracted on accompanying sides, and after frame 235 is positioned, they are then inserted into the upper ends of the protrusive grooves of the locigraph blocks 31, 32. The carriages of pins 41, 42 are then locked in place. Locigraph block 33, not shown in FIG. 20 but shown in FIG. 1, has its protrusive recording groove engaged by the pin 43. Frame 235 is then supported on the three pins.

The set of three locigraph blocks (as a unit) have therefore been positioned for information reconversion, starting from the three-dimensional static reference position (centric) as measured from the patient. However, the vertical centers of the locigraph blocks defining an axis HA' are somewhat misaligned relative to the axis HA of the drills and analog module. Both axes are shown in dotted lines in FIG. 20. The misalignment is exaggerated in the drawing for the purpose of illustration only.

The vertical adjustment screws 236 are then tightened to engage the associated surface of frame 235. Then the horizontal adjustment screws 237 are tightened to engage the frame 235. The screws 237 are then tightened further, one at a time, to provide a rigid support of the inner frame 230 from the outer frame 235.

Then the drills are energized. The upper frames 230, 235 are then manipulated as a unit, with the pins 41, 42, 43 riding in the tracks or grooves of the locigraph blocks. This process is continued until the recorded information has all been reconverted. If some of the information has been recorded on both sides of the locigraph blocks, the blocks are reversed in order to complete the procedure.

Figure 21:
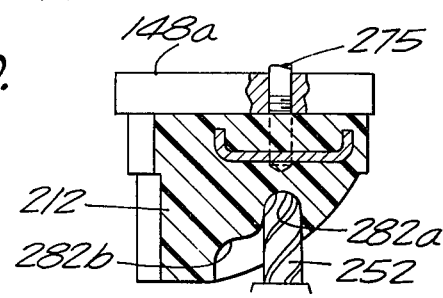
FIG. 21 is a fragmentary cross-sectional view taken on the line 21—21 of FIG. 20.

As a result of the reconversion procedure the reference openings 281a, 282a, are enlarged as shown in FIG. 21. In addition to the original openings 282a there are other pathways of movement such as that shown at 282b.

The reconverter instrument is disassembled, screws 275 are released, and the analog module M" is removed from the instrument.

INSTALLATION IN ARTICULATOR

Figure 22:
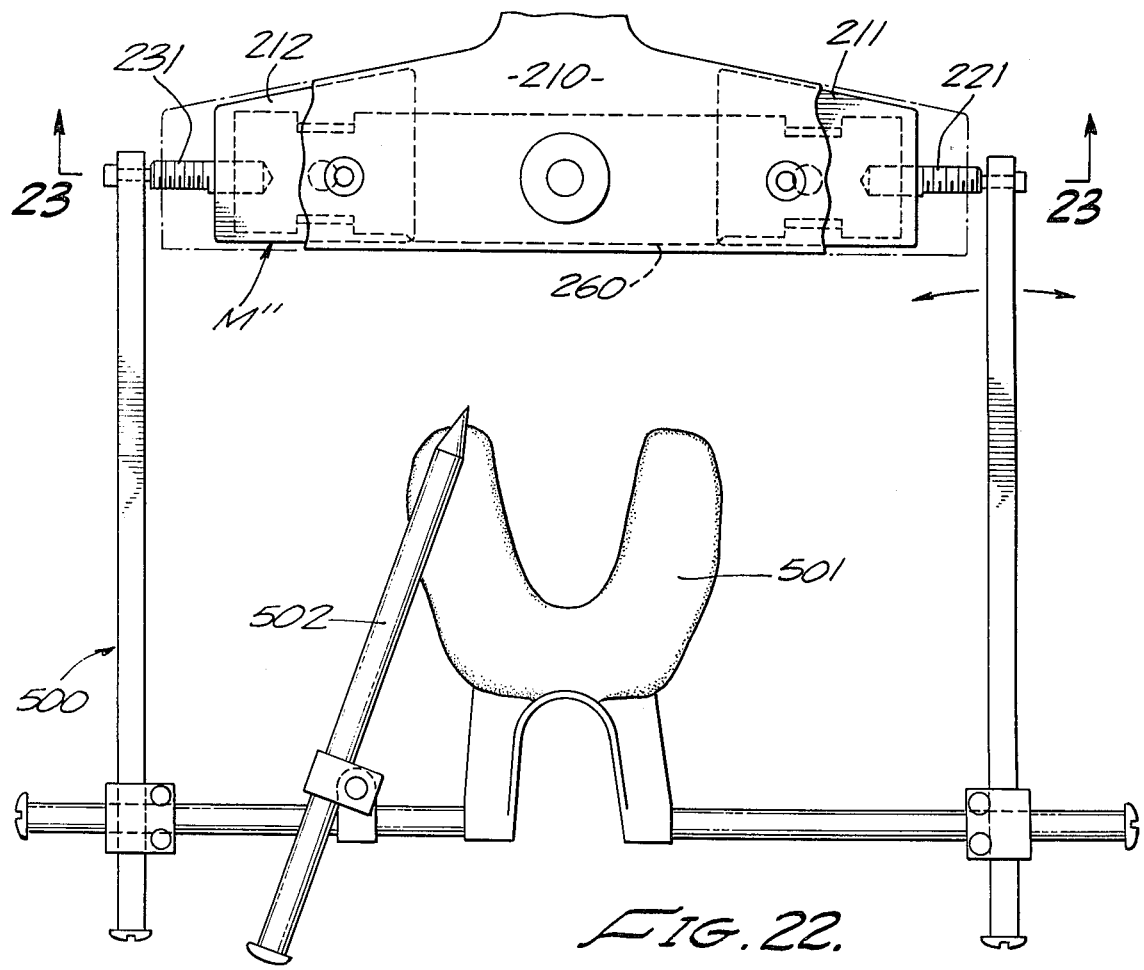
FIG. 22 is a top plan view, partially cut away, of the completed analog module of FIGS. 11 and 21 when positioned in an articulator and with a transfer face bow attached thereto.
Figure 27:
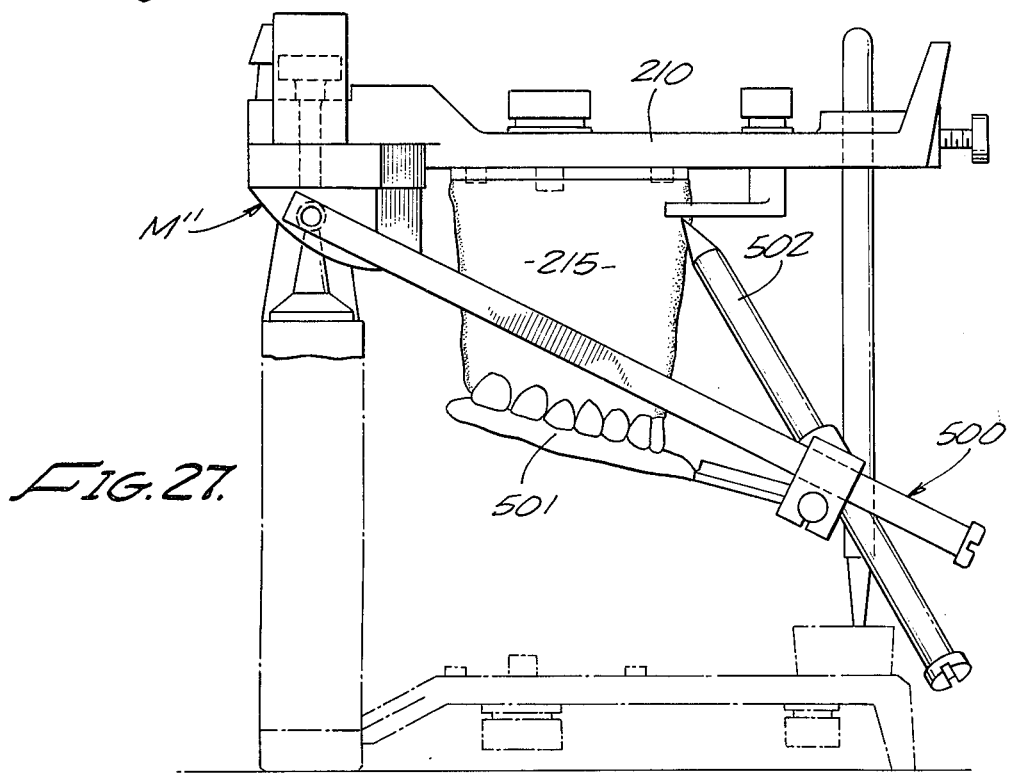
FIG. 27 is a plan view of the completed articulator set up including an upper dental cast mounted thereon.

Articulator upper frame 210 shown in FIGS. 22, 23, and 27 has openings which are spaced 100 mm apart, conforming to the threaded openings 263, 264 of the module. Analog module M" is placed under the articulator frame and fastened by means of the screws 275.

ALIGNMENT OF CASTS

A transfer face bow 500 (FIG. 22) may be used for aligning the casts. This is a conventional transfer face bow which is not capable of accomplishing a face width adjustment, except by loss of measurement accuracy. It has a bit plate 501, orbital pointer 502, and axis pointers 503, 504. When taking an impression from the patient on bite plate 501 the axis pointers 503, 504 are not necessarily collinear, but will in general have different axes. The pointer 504 is moved laterally through the openings 221a in the side wall of threaded tube 221. This avoids the necessity of lengthening or shortening the pointer 504, with the resultant loss of accuracy which would then occur. When the proper depth of the pointer is determined, set screw 222 is adjusted accordingly, using an allen wrench. The same procedure is followed with pointer 503. The side frames of the transfer face bow 500 are deflected slightly outwardly upon reinserting the pointers into the tubes and hooking them into the respective set screws.

It will be noted that each set screw besides having a standard socket to receive the allen wrench, also has a small conical opening at the bottom of that socket for receiving the pointer of the transfer face bow.

FIG. 23 is a cross-sectional elevational view of the simulated fossae showing how the transfer face bow pointers are received and retained by the set screws and threaded tubes. FIG. 27 is a side elevational view of the articulator showing the upper cast 215 in place. Positioning of the lower cast is completed in the conventional manner.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

What is claimed is:

1. An analog module for dental articulators, comprising:
    an elongated metallic support member adapted to fit underneath and in parallel relationship to either a reconverter instrument upper frame or an articulator upper frame, said support member having on each of its ends means for removable attachment thereof to a corresponding frame, said support member having adjacent each of its ends an integrally formed separate retaining means; and a pair of analog blocks made of a hard material capable of being milled, each of said blocks being disposed beneath said member and being attached to a respective one of said retaining means to be rigidly supported thereby, so that said member maintains a fixed lateral spacing of said blocks;

whereby when the module is attached to a reconverter instrument upper frame a pair of openings representing the jaw movement pattern of a patient may be formed in the lower sides of said blocks, and when the module is subsequently attached to an articulator upper frame the relative positions of said block openings remain unchanged.

2. An analog module as in claim 1 wherein said blocks are made of a hard plastic material and cast upon their respective retaining means to at least partially enclose the same.

3. An analog module as in claim 1 wherein said support member has essentially the configuration of a flat strap, and said attachment means includes a hole in each end of said strap.

4. An analog module as in claim 1 wherein said support member has essentially the configuration of a flat strap, each said retaining means including an opening formed in said strap, and each of said analog blocks being received within the corresponding opening.

5. An analog module as in claim 1 wherein
said support member has essentially the configuration of a flat strap,
said attachment means include a hole in each end of said strap,
said strap is deformed downwardly to provide a pedestal for each of said retaining means,
each of said retaining means includes an opening formed in the associated pedestal,
said analog blocks are made of a hard plastic material, and
each of said blocks is integrally cast upon the associated retaining means so as to fill and project through the associated opening.

6. An analog module for dental articulators, comprising:
an elongated metallic support member having essentially the configuration of a flat strap,
said member having a portion thereof adjacent each of is ends which is depressed downwardly to form a pedestal,
each of said pedestals having an opening formed therein,
the portion of said member intermediate said pedestals, having a flat upper surface which is adapted to bear against the flat under surface of either a reconverter instrument upper frame or an articulator upper frame;
a pair of analog blocks made of a hard plastic material, each of said blocks being integrally cast upon an associated one of said pedestals, so as to fill and project through the associaed opening thereof; and
means for removably attaching said support member to a corresponding instrument frame in a fixed position relative thereto;
whereby when the module is attached to a reconverter instrument upper frame a pair of openings representing the jaw movement pattern of a patient may be formed in the lower sides of said blocks, and upon subsequently attaching the module to an articulator upper frame the relative positions of said block openings remain unchanged.

7. An analog module as in claim 6 wherein said attachment means includes two holes spaced longitudinally on said strap.

8. An analog module as in claim 7 wherein said holes are in the end of said strap.

9. An analog module as in claim 7 which includes an additional hole in the longitudinal center of said strap, for receiving a centric locking device.

10. An analog module for use in dental articulators comprising:
an elongated metallic support member having a pair of longitudinally spaced holes therein for removably attaching said support member to an articulator frame in fixed relationship thereto; and
a pair of hard plastic blocks depending downwardly from respective ends of said support member, each block being integrally cast about a portion of said member in order to rigidly secure the same;
whereby a pair of openings formed in said blocks to represent a jaw movement pattern may be supported in precisely fixed relative positions.

11. In a dental articulator, the combination comprising:
a. a lower frame having a spaced pair of condyle spheres mounted in fixed positions thereon;
b. an upper frame;
c. an analog module including
1. an elongated metal support member having a spaced pair of retaining means formed thereon, and
2. a pair of hard plastic blocks at least partially encapsulating respective ones of said retaining means to thereby be held in fixed, spaced positions on said support member; and
d. fastening means removably securing said module suppot member to said upper frame;
said blocks having openings formed therein which cooperate with said spheres to reproduce the jaw movement pattern of a patient.

12. An analog module for use in a dental articulator, comprising:
a unitary structure including a pair of simulated fossae havin fixed lateral spacing therebetween, and means supporting said fossae in said fixed spacing;
means on said unitary structure for fastening same underneath the upper frame of either a reconverter instrument or the articulator in a predetermined, fixed position relative thereto;
each of said simulated fossae having formed in its under side a vertical reference opening whose upper end is hemispherical, the radius centers of said reference openings defining a hinge axis of the module; and
means on the external lateral sides of said simulated fossae indicating said hinge axis of the module and adapted for alignment of the hinge axis of a transfer face bow therewith.

13. An analog module as in claim 12 wherein said hinge axis alignment means includes a threaded opening in the lateral side of each of said fossae, and a threaded plug adjustably positioned in each said threaded opening; said two threaded openings having a common longitudinal axis.

14. An analog module as in claim 13 which includes a threaded tube forming one of said openings, said threaded tube projecting beyond the fossa wall and having a circumferential portion of its outer end cut away.

15. An analog module as in claim 12 wherein said unitary structure includes an elongated metal strap, and a pair of plastic blocks cast about the ends of said strap; said metal strap providing said supporting means, and said plastic blocks providing said fossae.

16. An analog module as in claim 12 wherein said fastening means includes a pair of holes formed in said supporting means and located intermediate to said simulated fossae.

17. The method of reproducing jaw movements in an articulator, one of whose frames carries a pair of spherical stylii, comprising the steps of:
  selecting a unitary relatively rigid module including a spaced pair of fossae and means supporting the fossae in spaced relationship, to simulate an upper jaw;
  applying a pair of hemispherically-ended drills to said fossae to form openings therein;
  enlarging said openings in accordance with a particular patient's jaw movements to be reproduced;
  thereafter attaching said module to the other frame of the articulator; and
  engaging said enlarged openings of the fossae with the spherical stylii of the one frame of the articulator.

18. An analog module for use in dental articulators comprising:
  an elongated metallic support member adapted to be horizontally disposed beneath the upper frame of an articulator in generally parallel relationship thereto;
  a pair of hard plastic blocks, each integrally cast about a corresponding end portion of said support member and depending downwardly therefrom to provide a corresponding fossa;
  each of said simulated fossae having formed in its under side a vertical reference opening, one portion of which conforms to a hemispherical shape;
  means on the laterally outward sides of said fossae indicating a line which extends through the radius centers of said hemispherical portions of both of said openings, said line thereby denoting a hinge axis of the module; and
  said module including means for fixedly attaching same to the articulator frame with the hinge axis of the module generally parallel to the frame.

* * * * *